United States Patent
Yarranton et al.

(10) Patent No.: US 9,109,032 B2
(45) Date of Patent: Aug. 18, 2015

(54) METHODS OF TREATING HEMATOLOGICAL PROLIFERATIVE DISORDERS BY TARGETING EPHA3 EXPRESSED ON ABERRANT VASCULATURE IN BONE MARROW

(75) Inventors: Geoffrey T. Yarranton, South San Francisco, CA (US); Varghese Palath, South San Francisco, CA (US); Christopher R. Bebbington, South San Francisco, CA (US); Mark Baer, South San Francisco, CA (US)

(73) Assignee: KaloBios Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 13/571,827

(22) Filed: Aug. 10, 2012

(65) Prior Publication Data
US 2013/0039907 A1 Feb. 14, 2013

Related U.S. Application Data

(60) Provisional application No. 61/523,104, filed on Aug. 12, 2011.

(51) Int. Cl.
*A61K 39/395* (2006.01)
*C07K 16/28* (2006.01)
*G01N 33/68* (2006.01)

(52) U.S. Cl.
CPC ........ *C07K 16/2866* (2013.01); *G01N 33/6863* (2013.01); *C07K 2317/33* (2013.01); *G01N 2333/715* (2013.01); *G01N 2800/52* (2013.01)

(58) Field of Classification Search
None
See application file for complete search history.

(56) References Cited

U.S. PATENT DOCUMENTS

| 2008/0286272 A1 | 11/2008 | Lackmann et al. |
| 2010/0226930 A1 | 9/2010 | Bebbington et al. |
| 2011/0123549 A1 | 5/2011 | Luehrsen et al. |

FOREIGN PATENT DOCUMENTS

WO WO 2010/102244 A1 9/2010

OTHER PUBLICATIONS

Palath et al. (Blood, 114(22: 688-688, 2009).*
Cilloni, D., et al., "EphA3 is abnormally expressed in chronic myeloprolipherative disorders and can be targeted by Dasatinib or by monoclonal antibodies," 12th Congress of the European Hematology Association, Jun. 7-10, 2007,*Haematologica*, vol. 92, Suppl : 248, Abstract 0665, 2 pgs.
Cilloni, D., et al., "EphA3 Kinase is Constitutively Activated in Chronic Myeloid Leukaemia during Progression to Accelerated and Blast Crisis and It Could Represent a New Molecular Target," *Blood*, vol. 112, Abstract 1092 (2008), ASH Annual Meeting Abstracts.
Frater et al., "Dysregulated angiogenesis in B-chronic lymphocytic leukemia: Morphologic, immunohistochemical, and flow cytometric evidence," *Diagnostic Pathol.*, vol. 3(16), 10 pgs.
Gianelli, U., et al., VEGF Expression Correlates with Microvessel Density in Philadelphia Chromosome-Negative Chronic Myeloproliferative Disorders, *Am J Clin Pathol*, vol. 128, pp. 966-973 (2007).
Guan, et al., "Copy Number Variations of EphA3 are Associated with Multiple Types of Hematologic Malignancies," *Clin Lymphoma Myeloma Leuk*, vol. 11(1), pp. 50-53 (Feb. 2011).
International Search Report and Written Opinion for PCT/US2012/050262 mailed Jan. 17, 2013, 16 pgs.
Kuzu et al, "Bone Marrow Microvessel Density (MVD) in Adult Acute Myeloid Leukemia (AML): Therapy Induced Changes and Effects on Survival ," *Leukemia and Lymphoma*, vol. 45:1185-1190 (2004).
Kvasnicka, H., et al., "Bone Marrow angiogenesis: methods of quantification and changes evolving in chronic myeloproliferative disorders," *Histol Histopathol.*, vol. 19, pp. 1245-1260 (2004).
Medinger, M., et al., "Clinical trials with anti-angiogenic agents in hematological malignancies," *J. Angiogenesis Res.*, vol. 2(10), 11 pgs. (2010).
Padró, T, et al., "Increases angiogenesis in the bone marrow of patients with acute myeloid leukemia," *Blood*, vol. 95(8), pp. 2637-2644 (Apr. 15, 2000).
Schuch et al., "Antiangiogenic treatment with endostatin inhibits progression of AML in vivo" *Leukemia* vol. 19:1312-1317 (2005).
Surawska, et al., "The role of ephrins and Eph receptors in cancer " *Cytokine Growth Factor Rev.*, vol. 15(6), pp. 419-433 (2004).

* cited by examiner

*Primary Examiner* — Misook Yu
*Assistant Examiner* — Nelson B Moseley, II
(74) *Attorney, Agent, or Firm* — Kilpatrick Townsend & Stockton LLP

(57) ABSTRACT

The invention provides diagnostic and therapeutic methods for the treatment of hematological proliferative disorders.

14 Claims, 2 Drawing Sheets

METHODS OF TREATING HEMATOLOGICAL PROLIFERATIVE DISORDERS BY TARGETING EPHA3 EXPRESSED ON ABERRANT VASCULATURE IN BONE MARROW

CROSS-REFERENCE TO RELATED APPLICATIONS

This application claims benefit of U.S. provisional application No. 61/523,104, filed Aug. 12, 2011, which application is herein incorporated by reference for all purposes.

REFERENCE TO A "SEQUENCE LISTING" SUBMITTED AS AN ASCII TEXT FILE

The sequence listing written in file SEQTXT_87142_004210US_847287.txt, created on Mar. 12, 2015; 5,917 bytes, machine format IBM-PC, MS-Windows operating system, is hereby incorporated by reference.

BACKGROUND OF THE INVENTION

EphA3 is a receptor tyrosine kinase that is expressed on the surface of certain solid tumors and on the vasculature of solid tumors (see, WO 2008/112192). In addition, EphA3 has been reported to be overexpressed on $CD34^+$ cells in chronic myeloid leukemia (CML) patients in the accelerated phase and blast crisis stage (Cilloni et al., American Society of Hematology, Abstract 1092, 2008). EphA3 is also expressed on the surface of neoplastic myeloid cells, including neoplastic myeloid stem cells, in the bone marrow and peripheral blood samples obtained from patients that have chronic myeloid leukemia (CML), acute myeloid leukemia (AML), chronic myelomonocytic leukemia (CMML), juvenile myelomonocytic leukemia (JMML), myelodysplastic syndrome (MDS), polycythemia vera (PV), essential thrombocythemia (ET), or idiopathic myelofibrosis (IM) (see, WO 2010/102244).

Angiogenesis is increased in bone marrow of AML and myelofibrosis patients (see, e.g., Padro et al., *Blood* 95:2637, 2000; Gianelli et al, *Am. J. Clin. Path.* 128:966, 2007) and high microvessel density is a poor prognostic factor in AML (e.g., Kukzu et al, *Leukemia and Lymphoma* 45:1185, 2004). Anti-angiogenic treatment with endostatin inhibits progression of AML in a mouse model (Schuch et al., *Leukemia* 19:1312, 2005). Further, new blood vessel formation is also observed in other hematological malignancies such as multiple myeloma, acute leukemias, and hematological proliferative neoplasms (see, e.g., Medinger & Mross, *J. Angiogenesis Res.* 2:10, 2010; and Frater et al., *Diagnostic Pathol.* 3:16, 2008).

BRIEF SUMMARY OF THE INVENTION

The invention is based, in part, on the discovery that vasculature in bone marrow from patients that have a hematological proliferative disorder express EphA3. Agents that target EphA3, such as activating EphA3 antibodies, can be employed for the treatment of hematological proliferative disorders in patients where the neoplastic cells themselves do not expression EphA3, or express low levels of EphA3. In some embodiments, the patient has chronic lymphocytic leukemia (CLL), chronic myeloid leukemia (CML), acute myeloid leukemia (AML), chronic myelomonocytic leukemia (CMML), juvenile myelomonocytic leukemia (JMML), multiple myeloma (MM), diffuse large B-cell lymphoma, non-Hodgkin lymphoma, mantle cell lymphoma (MCL), myelodysplastic syndrome (MDS), chronic neutrophilic leukemia, chronic eosinophilic leukemia, mast cell disease, polycythemia vera (PV), essential thrombocythemia (ET), or idiopathic myelofibrosis (IM).

It is the discovery of the inventors that EphA3 is selectively expressed on the aberrant vasculature in bone marrow of patients that have a hematological proliferative disorder. Thus, in one aspect, the invention provides a method of treating a patient that has a hematological proliferative disorder, the method comprising administering an anti EphA3 antibody to a patient that has a hematological proliferative disorder in which EphA3 is not expressed on the surface of the hematological proliferative disorder cells, or is expressed at low levels on the hematological proliferative disorder cells. In some embodiments, the patient has AML. In some embodiments, the patient has CML, CMML, JMML, MDS, PV, ET, or IM. In some embodiments, the patient has CLL, MM, diffuse large B-cell lymphoma, non-Hodgkin lymphoma (NHL), MCL, chronic neutrophilic leukemia, chronic eosinophilic leukemia, or mast cell disease. Not to be bound by theory, a therapeutic anti-EphA3 antibody kills cells, e.g., vascular endothelial cells, that express EphA3, but it is not necessarily anti-angiogenic in the sense that the antibody may not prevent proliferation of endothelial cells and angiogenesis.

In some embodiments, the therapeutic anti-EphA3 antibody multimerizes EphA3. In some embodiments, the therapeutic anti-EphA3 antibody activates EphA3 and causes morphological changes to target cells, e.g., rounding. In some embodiments, the therapeutic anti-EphA3 antibody kills the target cells by inducing antibody-dependent cell-mediated cytotoxicity (ADCC). In some embodiments, the therapeutic anti-EphA3 antibody (i) activates EphA3 and (ii) induces antibody-dependent cell-mediated cytotoxicity (ADCC).

In an additional aspect, the invention provides a method of treating a hematological proliferative disorder patient that has aberrant bone marrow vasculature that selectively expresses EphA3, but where the hematological proliferative disorder cells do not express EphA3 on the surface or express EphA3 at a low level, the method comprising administering a therapeutically effective amount of an anti-EphA3 antibody to the patient, wherein the anti-EphA3 antibody activates EphA3 and/or induces ADCC.

In some embodiments, the therapeutic anti-EphA3 antibody for use in the methods of the invention is a recombinant or chimeric antibody. In some embodiments, the therapeutic anti-EphA3 antibody is a human antibody. The therapeutic anti-EphA3 antibody may be a polyclonal antibody or a monoclonal antibody. In some embodiments, the therapeutic anti-EphA3 antibody is a multivalent antibody that comprises a Fab, a Fab', or an Fv. In some embodiments, the antibody is a $F(ab')_2$. In some embodiments, the therapeutic anti-EphA3 antibody competes for EphA3 binding with mAb IIIA4. In some embodiments, the therapeutic antibody binds to the same epitope as mAb IIIA4. In typical embodiments, the therapeutic antibody does not block ephrin ligand binding, e.g., ephrinA5 binding, to EphA3. In some embodiments the therapeutic anti-EphA3 antibody comprises the $V_H$ and $V_L$ regions of mAb IIIA4. In some embodiments, the therapeutic anti EphA3 antibody comprises the $V_H$ and $V_L$ region CDR1, CDR2 and CDR3 of mAb IIIA4. In some embodiments, the therapeutic antibody comprises the $V_H$ region CDR3 and $V_L$ region CDR3 of mAb IIIA4. In some embodiments, the therapeutic antibody induces ADCC. Thus, in some embodiments the therapeutic antibody has an active isotype, e.g., the antibody has a human heavy chain constant region that is a gamma-1 or gamma-3 region. In some embodiments, the therapeutic antibody does not induce ADCC, e.g., the antibody has a human heavy chain constant region that is a gamma-2 or gamma-4 region, or is a multimeric fragment.

In the context of this invention, "an anti-EphA3 antibody that activates EphA3 or induces ADCC" refers to an antibody that (i) activates EphA3 (ii) induces ADCC, or (iii) activates and induces ADCC.

In some embodiments of the invention, a hematological proliferative disorder patient is treated with an anti-EphA3 antibody as described herein and also receives treatment with another therapeutic agent for the disease. Thus, in some embodiments, the method comprises administering one or more additional therapeutic agents. For example, when the hematological proliferative disorder is CML, additional therapeutic agents may include imatinib mesylate, nilotinib, dasatinib, or another chemotherapeutic agent. When the hematological proliferative disorder is AML, the additional therapeutic agents may be, e.g., cytosine arabinoside alone or in combination with daunorubicin.

In additional aspects, the invention provides a method of identifying a hematological proliferative disorder patient having a hematological proliferative disorder that is a candidate for treatment with an anti-EphA3 antibody, wherein the method comprises detecting EphA3 expression on the aberrant bone marrow vasculature in the hematological proliferative disorder patient In some embodiments, the patient has AML. In some embodiments, the patient has CML, CMML, JMML, MDS, PV, ET, or IM. In some embodiments, the patient has CLL, MM, diffuse large B-cell lymphoma, NHL, MCL, chronic neutrophilic leukemia, chronic eosinophilic leukemia, or mast cell disease.

In some embodiments, the invention provides a method of monitoring the efficacy of treatment of a hematological proliferative disorder patient that has aberrant bone marrow vasculature that expresses EphA3, the method comprising: obtaining a bone marrow sample from a patient that has been treated with a therapeutic agent for the hematological proliferative disorder; and detecting expression of EphA3 on the aberrant bone marrow vasculature.

EphA3 expression can be detected using commonly known techniques. Thus, in some embodiments detecting expression of EphA3 comprises detecting protein expression on the vasculature, e.g., using immunohistochemistry. In some embodiments, an antibody used to detect EphA3 expression on aberrant vasculature binds to an epitope different from the epitope that is bound by the therapeutic antibody. In some embodiments, the antibody is the monoclonal antibody SL-2, which is produced by a hybridoma deposited with the American Type Culture Collection (ATCC), 10801 University Blvd., Manassas, Va. 20110, USA on Nov. 8, 2011 under the conditions of the Budapest Treaty and assigned patent deposit number PTA-12227. In some embodiments, the antibody is the monoclonal antibody SL-7, which is produced by a hybridoma deposited with ATCC on Nov. 8, 2011 under the conditions of the Budapest Treaty and assigned patent deposit number PTA-12228.

In a further aspect, the invention provides monoclonal antibodies, e.g., for detection of EphA3 expression on aberrant vasculature. In one embodiment, the monoclonal antibody SL-2, which is produced by a hybridoma deposited under ATCC deposit number PTA-12227. In one embodiment, the monoclonal antibody is SL-7, which is produced by a hybridoma deposited under ATCC deposit number PTA-12228. The invention additional provides kits that include a monoclonal antibody SL-2 and/or SL-7. Such kits can, e.g., also contain additional reagents, such as reagents for immunohistochemical analysis.

DETAILED DESCRIPTION OF THE INVENTION

Definitions

Figure 1:
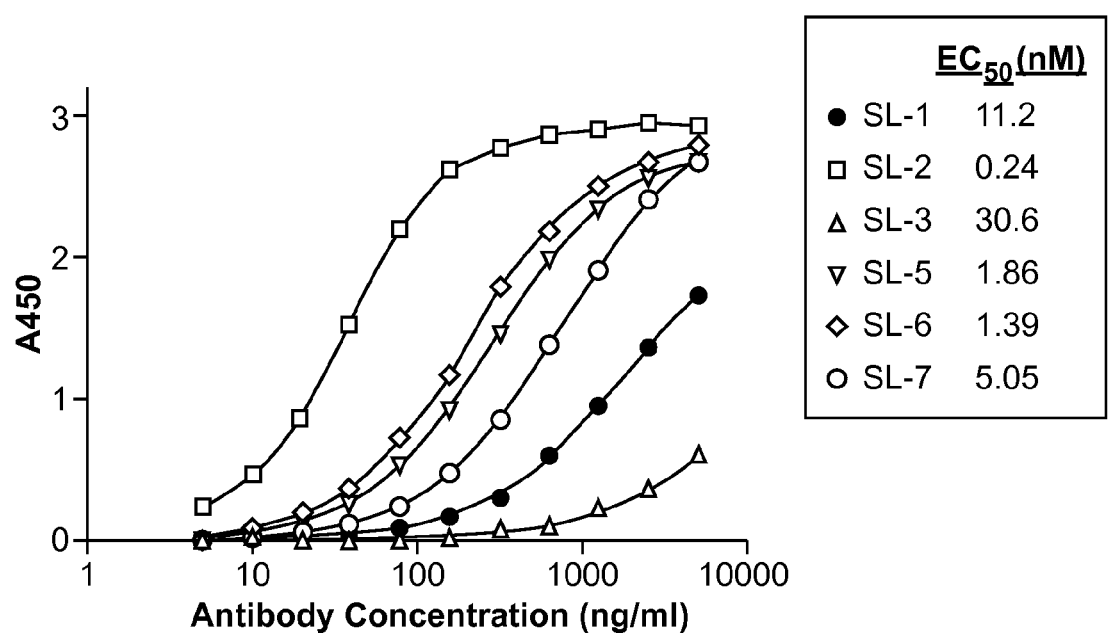
FIG. 1 provides illustrative data from an ELISA demonstrating antibody binding to EphA3. Supernatants from six hybridomas were diluted in PBS to 5 µg/ml and applied to EphA3 coated plates. Binding was detected with a goat anti mouse HRP conjugate. Data were analyzed with Prizm 5.0 software.

The term "hematological proliferative disorders" as used herein refers to certain diseases that involve abnormal proliferation of hematological cells, including leukemias, lymphomas, and various myeloid neoplasias and dysplasias. In the current invention, hematological proliferative diseases thus include chronic hematological proliferative disorders (CMPDs); acute myeloid leukemia (AML); chronic myelomonocytic leukemia (CMML); juvenile myelomonocytic leukemia (JMML), chronic lymphocytic leukemia (CLL), chronic myeloid leukemia (CML), multiple myeloma (MM), diffuse large B-cell lymphoma, non-Hodgkin lymphoma (NHL), mantle cell lymphoma (MCL), myelodysplastic syndrome (MDS), chronic neutrophilic leukemia, chronic eosinophilic leukemia, mast cell disease, polycythemia vera (PV), essential thrombocythemia (ET), and idiopathic myelofibrosis (IM). The term "JMML" encompasses all diagnoses referred to as Juvenile Chronic Myeloid Leukemia (JCML), Chronic Myelomonocytic Leukemia of Infancy, and Infantile Monosomy 7 Syndrome. Hematological proliferative disorders can be diagnosed using known criteria, e.g., the World Health Organization (WHO) criteria, the French-American-British (FAB) classification system, the International Prognostic Scoring System (IPSS), and the like. In the 2008 WHO classification, CMPDs are referred to as hematological proliferative neoplasms (MPNs). Hematological proliferative disorders are often characterized by the presence of particular mutations. For example, CML is characterized by the presence of BCR-ABL. PV, ET, and IM are "non-BCR-ABL" (also referred to herein as "BCR-ABL minus" or "BCR-ABL negative") CMPDs, as these disorders do not have BCR-ABL. However, BCR-ABL negative disorders are often characterized by the presence of JAK2 mutations, which are rare in CML. As used herein, the term "CML" includes both Philadelphia chromosome positive and Philadelphia chromosome negative CML.

The term "hematological proliferative disorder cells" as used in the context of this invention refers to neoplastic hematological cells that are characteristic of a hematological proliferative disorder. The term "neoplastic" encompasses cells that may not yet be considered to be malignant, e.g., such as the myeloid cells that are characteristic of myelodysplastic syndrome, as well as malignant cells, such as malignant acute leukemia cells. "Hematological proliferative disorder cells" encompasses both blast cells and stem cells, but does not include aberrant bone marrow vasculature associated with the aberrant angiogenesis that occurs in the bone marrow of patients that have a hematological proliferative disorder, e.g., AML patients.

As used in the context of this application, "aberrant bone marrow angiogenesis" refers to increased, and structurally abnormal, angiogenesis relative to the level of angiogenesis in normal bone marrow and the structure of the vasculature in normal bone marrow. As used herein "aberrant vasculature" refers to anomalies of microvascular architecture including: enhanced irregularity of shape and tortuosity, increased fibers, increased microvessel density, and complex branching of irregular shaped sinuses (see, e.g., Kvansnicka & Thlele, *Histol. Pathol.* 19:1245-1260, 2004).

The term "selectively expressed" as applied to EphA3 expression in the context of expression or "selective expression of EphA3" on aberrant vasculature refers to EphA3 expression on abnormal vasculature, but not normal vasculature. EphA3 can be expressed in the endothelium of the abnormal vasculature or in other parts of vessels, e.g., the tunica media or tunica externa.

In the context of this invention, "low level" or "minimal" expression of EphA3 on hematological proliferative disorder cells refers to expression in a population of cells such that less than 50%, or in some embodiments, less than 40%, 30%, 20%, 10%, or less than 5%, of the hematological proliferative disorder cells express EphA3 as assessed by flow cytometry or other means known in the art. In some embodiments, hematological proliferative disorder cells in CML, PV, ET, IM, AML, MDS, CMML, or JMML exhibit low level expression of EphA3, where EphA3 is expressed at a level of 5% or less of the hematological proliferative disorder cell population as assessed by flow cytometry.

The term "EphA3+" when used in the context of expression on aberrant vasculature refers to EphA3 expression that is above background. The term "substantially Epha3−" in the context of expression of EphA3 on neoplastic hematological disorder cells refers to no expression, i.e., where expression is not observed on any of the cells or where less than 50%, typically less than 40%, less than 30%, less than 20%, less than 10% or less than 5% of the neoplastic cells express EphA3.

The terms "cancer cell" or "tumor cell" are used interchangeably to refer to a neoplastic cell. The term includes cells that are benign as well as malignant. Neoplastic transformation is associated with phenotypic changes of the tumor cell relative to the cell type from which it is derived. The changes can include morphological changes, and aberrant growth. (see, Freshney, *Culture of Animal Cells a Manual of Basic Technique* (3$^{rd}$ edition, 1994).

"Inhibiting growth of hematological proliferative disorder cells" in the context of the invention refers to slowing growth and/or reducing the cancer cell burden of a patient that has a hematological proliferative disorder. "Inhibiting growth of a cancer", e.g., AML, thus includes killing cancer cells.

As used herein "EphA3" refers to the Eph receptor A3. This receptor has also been referred to as "Human embryo kinase", "hek", "eph-like tyrosine kinase 1", "etk1" or "tyro4". EphA3 belongs to the ephrin receptor subfamily of the protein-tyrosine kinase family. EPH and EPH-related receptors have been implicated in mediating developmental events. Receptors in the EPH subfamily typically have a single kinase domain and an extracellular region containing a Cys-rich domain and 2 fibronectin type III repeats. The ephrin receptors are divided into 2 groups based on the similarity of their extracellular domain sequences and their affinities for binding ephrin-A and ephrin-B ligands. EphA3 binds ephrin-A ligands. EphA3 nucleic acid and protein sequences are known. An example of a human EphA3 amino acid sequence is available under accession number EAW68857.

In the context of this invention, "an anti-EphA3 antibody that activates EphA3 or induces ADCC" refers to an antibody that (i) activates EphA3 (ii) induces ADCC, or (iii) activates and induces ADCC.

For the purposes of the present invention, "activation" of EphA3 causes phosphorylation of EphA3. An antibody that activates EphA3 or "an activating antibody" causes phosphorylation of EphA3 and shape change, e.g., rounding, of endothelial cells and is therefore considered to be an agonist in the context of this invention. EphA3 can be activated by dimerization, which leads to shape change, e.g., rounding, in endothelial cells and may lead to apoptosis. In some embodiments, an antibody that activates EphA3 competes with mAb IIIA4 for binding to EphA3. Typically, an "activating" antibody binds to the ligand binding domain (amino acids 29-202 of EphA3) wherein amino acid residues 131, 132, and 136 are important for binding. In some embodiments, the activating antibody binds to a site encompassing the residues 131, 132, and 136 within the ligand binding domain of human EphA3 protein.

In the present application, the terms "EphA3 antibody" or "anti-EphA3 antibody" are used interchangeably to refer to an antibody that specifically binds to EphA3. In some embodiments, the antibody can dimerize EphA3. The term encompasses antibodies that bind to EphA3 in the presence of ephrin ligand (e.g., ephrin-A5) binding, as well as antibodies that bind to the ligand binding site.

An "EphA3 antibody that binds to EphA3 in the presence of binding of an ephrin ligand" refers to an antibody that does not significantly prevent binding of an ephrin ligand, such as ephrin-A5, to EphA3. The presence of such an antibody in a binding reaction comprising EphA3 and an ephrin ligand, e.g., ephrin-A5, reduces ephrin ligand binding to EphA3 by less than about 30%, typically less than 20% or 10%.

The term "mAb IIIA4" refers to monoclonal antibody IIIA4 that was originally raised against LK63 human acute pre-B leukemia cells to affinity isolate EphA3 (Boyd, et al. *J Biol Chem* 267:3262-3267, 1992). mAb IIIA4 binds to the native EphA3 globular ephrin-binding domain (e.g., Smith, et al., *J. Biol. Chem* 279:9522-9531, 2004). It is deposited in the European Collection of Animal Cell Cultures under accession no. 91061920 (see, e.g., EP patent no. EP0590030).

An "antibody having an active isotype" as used herein refers to an antibody that has a human Fc region that binds to an Fc receptor present on immune effector cells. "Active isotypes" include IgG1, IgG3, IgM, IgA, and IgE. The term encompasses antibodies that have a human Fc region that comprises modifications, such as mutations or changes to the sugar composition and/or level of glycosylation, that modulate Fc effector function.

An "Fc region" refers to the constant region of an antibody excluding the first constant region immunoglobulin domain. Thus, Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cγ2 and Cγ3 and the hinge between Cγ1 and Cγ. It is understood in the art that the boundaries of the Fc region may vary, however, the human IgG heavy chain Fc region is usually defined to comprise residues C226 or P230 to its carboxyl-terminus, using the numbering is according to the EU index as in Kabat et al. (1991, NIH Publication 91-3242, National Technical Information Service, Springfield, Va.). The term "Fc region" may refer to this region in isolation or this region in the context of an antibody or antibody fragment. "Fc region" includes naturally occurring allelic variants of the Fc region as well as modifications that modulate effector function. Fc regions also include variants that don't result in alterations to biological function. For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, et al., *Science* 247:306-1310, 1990).

As used herein, an "antibody" refers to a protein functionally defined as a binding protein and structurally defined as comprising an amino acid sequence that is recognized by one of skill as being derived from the framework region of an immunoglobulin encoding gene of an animal producing antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

The term "antibody" as used herein includes antibody fragments that retain binding specificity. For example, there are a number of well characterized antibody fragments. Thus, for example, pepsin digests an antibody C-terminal to the disulfide linkages in the hinge region to produce F(ab')$_2$, a dimer of Fab which itself is a light chain joined to VH-CH1 by a disulfide bond. The F(ab')$_2$ may be reduced under mild conditions to break the disulfide linkage in the hinge region thereby converting the (Fab')$_2$ dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody, as used herein also includes antibody fragments either produced by the modification of whole antibodies or synthesized using recombinant DNA methodologies.

Antibodies include $V_H$-$V_L$ dimers, including single chain antibodies (antibodies that exist as a single polypeptide chain), such as single chain Fv antibodies (sFv or scFv) in which a variable heavy and a variable light region are joined together (directly or through a peptide linker) to form a continuous polypeptide. The single chain Fv antibody is a covalently linked $V_H$-$V_L$ which may be expressed from a nucleic acid including $V_H$- and $V_L$-encoding sequences either joined directly or joined by a peptide-encoding linker (e.g., Huston, et al. *Proc. Nat. Acad. Sci. USA*, 85:5879-5883, 1988). While the $V_H$ and $V_L$ are connected to each as a single polypeptide chain, the $V_H$ and $V_L$ domains associate non-covalently. Alternatively, the antibody can be another fragment. Other fragments can also be generated, e.g., using recombinant techniques, as soluble proteins or as fragments obtained from display methods. Antibodies can also include diantibodies and miniantibodies. Antibodies of the invention also include heavy chain dimers, such as antibodies from camelids. For the purposes of this inventor, antibodies are employed in a form that can activate EphA3 present on the surface of hematological proliferative cells or that can kill hematological proliferative cells by ADCC. Thus, in some embodiments an antibody is dimeric. In other embodiments, the antibody may be in a monomeric form that has an active isotype. In some embodiments the antibody is in a multivalent form, e.g., a trivalent or tetravalent form, that can cross-link EphA3.

As used herein, "V-region" refers to an antibody variable region domain comprising the segments of Framework 1, CDR1, Framework 2, CDR2, and Framework3, including CDR3 and Framework 4, which segments are added to the V-segment as a consequence of rearrangement of the heavy chain and light chain V-region genes during B-cell differentiation.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

The sequences of the framework regions of different light or heavy chains are relatively conserved within a species. The framework region of an antibody, that is the combined framework regions of the constituent light and heavy chains, serves to position and align the CDRs in three dimensional space.

The amino acid sequences of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. *J. Mol. Biol.* 196, 901-917; Chothia C. et al., 1989, Conformations of immunoglobulin hypervariable regions. Nature 342, 877-883; Chothia C. et al., 1992, structural repertoire of the human VH segments J. Mol. Biol. 227, 799-817; Al-Lazikani et al., *J. Mol. Biol* 1997, 273(4)). Definitions of antigen combining sites are also described in the following: Ruiz et al., IMGT, the international ImMunoGeneTics database. *Nucleic Acids Res.*, 28, 219-221 (2000); and Lefranc, M.-P. IMGT, the international ImMunoGeneTics database. *Nucleic Acids Res.* January 1; 29(1):207-9 (2001); MacCallum et al, Antibody-antigen interactions: Contact analysis and binding site topography, *J. Mol. Biol.*, 262 (5), 732-745 (1996); and Martin et al, *Proc. Natl Acad. Sci. USA*, 86, 9268-9272 (1989); Martin, et al, *Methods Enzymol.*, 203, 121-153, (1991); Pedersen et al, *Immunomethods*, 1, 126, (1992); and Rees et al, In Sternberg M. J. E. (ed.), Protein Structure Prediction. Oxford University Press, Oxford, 141-172 1996).

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

As used herein, "chimeric antibody" refers to an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region, or portion thereof, having a different or altered antigen specificity; or with corresponding sequences from another species or from another antibody class or subclass.

As used herein, "humanized antibody" refers to an immunoglobulin molecule in CDRs from a donor antibody are grafted onto human framework sequences. Humanized antibodies may also comprise residues of donor origin in the framework sequences. The humanized antibody can also comprise at least a portion of a human immunoglobulin constant region. Humanized antibodies may also comprise residues which are found neither in the recipient antibody nor in the imported CDR or framework sequences. Humanization can be performed using methods known in the art (e.g., Jones et al., Nature 321:522-525; 1986; Riechmann et al., Nature 332:323-327, 1988; Verhoeyen et al., Science 239:1534-1536, 1988); Presta, Curr. Op. Struct. Biol. 2:593-596, 1992; U.S. Pat. No. 4,816,567), including techniques such as "superhumanizing" antibodies (Tan et al., J. Immunol. 169: 1119, 2002) and "resurfacing" (e.g., Staelens et al., Mol. Immunol. 43: 1243, 2006; and Roguska et al., Proc. Natl. Acad. Sci USA 91: 969, 1994).

A "HUMANEERED™" antibody in the context of this invention refers to an engineered human antibody having a binding specificity of a reference antibody. An engineered human antibody for use in this invention has an immunoglobulin molecule that contains minimal sequence derived from a donor immunoglobulin. In some embodiments, the engineered human antibody may retain only the minimal essential binding specificity determinant from the CDR3 regions of a reference antibody. Typically, an engineered human antibody is engineered by joining a DNA sequence encoding a binding specificity determinant (BSD) from the CDR3 region of the heavy chain of the reference antibody to human $V_H$ segment sequence and a light chain CDR3 BSD from the reference antibody to a human $V_L$ segment sequence. A "BSD" refers to a CDR3-FR4 region, or a portion of this region that mediates binding specificity. A binding specificity determinant therefore can be a CDR3-FR4, a CDR3, a minimal essential binding specificity determinant of a CDR3 (which refers to any region smaller than the CDR3 that confers binding specificity when present in the V region of an antibody), the D segment (with regard to a heavy chain region), or other regions of CDR3-FR4 that confer the binding specificity of a reference antibody. Methods for engineering human antibodies are provided in U.S. Pat. No. 7,981,843 and US patent application publication no. 20060134098.

The term "human antibody" as used herein refers to an antibody that is substantially human, i.e., has FR regions, and often CDR regions, from a human immune system. Accordingly, the term includes humanized and HUMANEERED™ antibodies as well as antibodies isolated from mice reconstituted with a human immune system and antibodies isolated from display libraries.

A "hypofucosylated" antibody preparation refers to an antibody preparation in which the average content of α1,6-fucose is less than 50% of that found in naturally occurring IgG antibody preparations. As understood in the art, "hypofucosylated" is used in reference to a population of antibodies.

An "afucosylated" antibody lacks α1,6-fucose attached to the CH2 domain of the IgG heavy chain.

A "therapeutic" antibody as used herein refers to a human and/or chimeric antibody that is administered to a patient that has a hematological proliferative disorder.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid. Similarly, a heterologous protein will often refer to two or more subsequences that are not found in the same relationship to each other in nature.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

The phrase "specifically (or selectively) binds" to an antibody or "specifically (or selectively) immunoreactive with," when referring to a protein or peptide, refers to a binding reaction where the antibody binds to the protein of interest. In the context of this invention, the antibody typically binds to EphA3 with an affinity that is at least 100-fold better than its affinity for other antigens.

The term "equilibrium dissociation constant ($K_D$) refers to the dissociation rate constant ($k_d$, time$^{-1}$) divided by the association rate constant ($k_a$, time$^{-1}$, M$^{-1}$). Equilibrium dissociation constants can be measured using any known method in the art. The antibodies of the present invention are high affinity antibodies. Such antibodies have an affinity better than 500 nM, and often better than 50 nM or 10 nM. Thus, in some embodiments, the antibodies of the invention have an affinity in the range of 500 nM to 100 pM, or in the range of 25 nM to 100 pM, or in the range of 25 nM to 50 pM, or in the range of 25 nM to 1 pM.

As used herein, "hematological proliferative disorder therapeutic agent" refers to an agent that when administered to a patient suffering from a hematological proliferative disorder, e.g., AML, in a therapeutically effective dose, will cure, or at least partially arrest the symptoms of the disease and complications associated with the disease. In some embodiments, the therapeutic agent may be a chemotherapeutic agent.

The terms "identical" or percent "identity," in the context of two or more polypeptide (or nucleic acid) sequences, refer to two or more sequences or subsequences that are the same or have a specified percentage of amino acid residues (or nucleotides) that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site). Such sequences are also referred to herein as being "substantially identical." "Substantially identical" sequences also includes sequences that have deletions and/or additions, as well as those that have substitutions, as well as naturally occurring, e.g., polymorphic or allelic variants, and manmade variants. As described below, the preferred algorithms can account for gaps and the like. Preferably, protein sequence identity exists over a region that is at least about 25 amino acids in length, or more preferably over a region that is 50-100 amino acids=in length, or over the length of a protein.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Preferred examples of algorithms that are suitable for determining percent sequence identity and sequence similarity include the BLAST and BLAST 2.0 algorithms, which are described in Altschul et al., *Nuc. Acids Res.* 25:3389-3402 (1977) and Altschul et al., *J. Mol. Biol.* 215:403-410 (1990). BLAST and BLAST 2.0 are used, with the parameters described herein, to determine percent sequence identity for the nucleic acids and proteins of the invention. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

An indication that two polypeptides are substantially identical is that the first polypeptide is immunologically cross reactive with the antibodies raised against the second polypeptide. Thus, a polypeptide is typically substantially identical to a second polypeptide, e.g., where the two peptides differ only by conservative substitutions.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" in some embodiments denotes that a protein gives rise to essentially one band in an electrophoretic gel. Preferably, it means that the protein is at least 85% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid that encode a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The term "a" or "an" is generally intended to mean "one or more" unless otherwise indicated.

Introduction

The invention is based, in part, on the discovery that bone marrow vasculature that arises from aberrant angiogenesis in patients that have a hematological proliferative disorder, e.g., AML, CML, CMML, JMML, MDS, PV, ET, IM, CLL, MM, diffuse large B-cell lymphoma, NHL, MCL, chronic neutrophilic leukemia, chronic eosinophilic leukemia, or mast cell disease, selectively express EphA3. EphA3 expression in the aberrant vasculature is often in the endothelial layer of the neovasculature, but may also be observed in the extraendothelial layer of larger vessels, e.g., in the tunica media and/or tunica externa. Thus, patients that have a hematological proliferative disorder in which the hematological proliferative disorder cells do not express EphA3, or express EphA3 at a low level, can be treated by administering an anti-EphA3 activating antibody and/or an anti-EphA3 antibody that induces ADCC. Accordingly, in one aspect, the invention provides methods of treating a CML, PV, ET, IM, AML, MDS, CMML, or JMML patient where the patient does not express EphA3 on hematological proliferative disorder cells or expresses EphA3 at a level of 5% or less, comprising administering an activating anti-EphA3 antibody to the patient. In some embodiments, the patient has AML. In some embodiments, the patient has CML, CMML, JMML, MDS, PV, ET, or IM. In some embodiments, the patient has CLL, MM, diffuse large B-cell lymphoma, NHL, MCL, chronic neutrophilic leukemia, chronic eosinophilic leukemia, or mast cell disease. In some embodiments, the methods of the invention comprise administering an anti-EphA3 antibody that induces ADCC to a CML, PV, ET, IM, AML, MDS, CMML, or JMML patient where the patient does not express EphA3 on hematological proliferative disorder cells. In some embodiments, an anti-EphA3 antibody that is administered to a CML, PV, ET, IM, AML, MDS, CMML, or JMML patient that does not express EphA3 on hematological proliferative disorder cells (i) is an activating anti-EphA3 antibody and (ii) induces ADCC.

In some embodiments, an anti-EphA3 antibody for use in this invention does not block binding of EphA3 to ephrin, e.g., ephrin-A5. In some embodiments, the antibody dimerizes EphA3. In some embodiments, the antibody cross-links EphA3. In some embodiments, the antibody competes with mAb IIIA4 for binding to EphA3, e.g., such an antibody may bind to the same epitope as mAb IIIA4. In some embodiments, the antibody has an active isotype where the heavy chain constant domain can bind to Fc receptor present on immune effector cells, leading to ADCC.

Therapeutic Anti EphA3 Antibodies

The anti-EphA3 antibodies for use in the methods of the invention can be raised against EphA3 proteins, or fragments, or produced recombinantly. Any number of techniques can be used to determine antibody binding specificity. See, e.g., Harlow & Lane, Antibodies, A Laboratory Manual (1988) for a description of immunoassay formats and conditions that can be used to determine specific immunoreactivity of an antibody In some embodiments, the anti-EphA3 antibody is a polyclonal antibody. Methods of preparing polyclonal antibodies are known to the skilled artisan (e.g., Harlow & Lane, Antibodies, A Laboratory manual (1988); Methods in Immunology). Polyclonal antibodies can be raised in a mammal by one or more injections of an immunizing agent and, if desired, an adjuvant. The immunizing agent includes a EphA3 receptor protein, or fragment thereof.

In some embodiments, the anti-EphA3 antibody is a monoclonal antibody. Monoclonal antibodies may be prepared using hybridoma methods, such as those described by Kohler & Milstein, Nature 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

Human monoclonal antibodies can be produced using various techniques known in the art, including phage display libraries (Hoogenboom & Winter, J. Mol. Biol. 227:381 (1991); Marks et al., J. Mol. Biol. 222:581 (1991)). The techniques of Cole et al. and Boerner et al. are also available for the preparation of human monoclonal antibodies (Cole et al., Monoclonal Antibodies and Cancer Therapy, p. 77 (1985) and Boerner et al., J. Immunol. 147(1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); Lonberg & Huszar, Intern. Rev. Immunol. 13:65-93 (1995).

In some embodiments the anti-EphA3 antibodies are chimeric or humanized monoclonal antibodies. As noted supra, humanized forms of antibodies are chimeric immunoglobulins in which a CDR of a human antibody is replaced by a CDR of a non-human species such as mouse, rat or rabbit having the desired specificity, affinity and capacity.

An antibody that is employed in the invention can be in numerous formats. In some embodiments, the antibody can include an Fc region, e.g., a human Fc region. For example, such antibodies include IgG antibodies that bind EphA3 and that have an active isotype. In some embodiments, the antibody can be an active fragment (e.g., it can dimerize EphA3) or can comprise a derivative of an antibody such as an Fab, Fab', F(ab')$_2$, Fv, scFv, or a single domain antibody ("dAb"). For example, in some embodiments, the antibody may be a F(ab')$_2$. Other exemplary embodiments of antibodies that can be employed in the invention include activating nanobodies or activating camellid antibodies. Such antibodies may additionally be recombinantly engineered by methods well known to persons of skill in the art. As noted above, such antibodies can be produced using known techniques. As appreciated by one of skill in the art, in some embodiments when an antibody is in a format that can be monovalent, e.g., an Fv or Fab format, the antibody may be employed as a multivalent antibody, such as a trivalent or tetravalent antibody. Methods of generating multivalent antibodies are known (see, e.g., King et al., *Cancer Res.* 54:6176-6185, 1994).

In many embodiments, an antibody for use in the invention has an Fc constant region that has an effector function, e.g., binds to an Fc receptor present on immune effector cells. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g., B cell receptor), and the like. Such effector functions generally require the Fc region to be combined with a binding domain (e.g. an antibody variable domain) and can be assessed using known assays (see, e.g., the references cited hereinbelow.)

Anti-EphA3 antibodies that have an active isotype and are bound to Fc-receptors on effector cells, such as macrophages, monocytes, neutrophils and NK cells, can induce cell death by ADCC.

The Fc region can be from a naturally occurring IgG1, or other active isotypes, including IgG3, IgM, IgA, and IgE. "Active isotypes" include antibodies where the Fc region comprises modifications to increase binding to the Fc receptor or otherwise improve the potency of the antibody. Such an Fc constant region may comprise modifications, such as mutations, changes to the level of glycosylation and the like, that increase binding to the Fc receptor. There are many methods of modifying Fc regions that are known in the art. For example, U.S. Patent Application Publication No. 20060039904 describes variants of Fc receptors that have enhanced effector function, including modified binding affinity to one or more Fc ligands (e.g., FcγR, C1q). Additionally, such Fc variants have altered antibody-dependent cell-mediated cytotoxicity (ADCC) and/or complement dependent cytotoxicity (CDC) activity. Other Fc variants include those disclosed by Ghetie et al., *Nat Biotech.* 15:637-40, 1997; Duncan et al, *Nature* 332:563-564, 1988; Lund et al., *J. Immunol* 147:2657-2662, 1991; Lund et al, *Mol Immunol* 29:53-59, 1992; Alegre et al, *Transplantation* 57:1537-1543, 1994; Hutchins et al., *Proc Natl. Acad Sci USA* 92:11980-11984, 1995; Jefferis et al, *Immunol Lett.* 44:111-117, 1995; Lund et al., *FASEB J* 9:115-119, 1995; Jefferis et al, *Immunol Lett* 54:101-104, 1996; Lund et al, *J Immunol* 157:4963-4969, 1996; Armour et al., *Eur J Immunol* 29:2613-2624, 1999; Idusogie et al, *J Immunol* 164:4178-4184, 200; Reddy et al, *J Immunol* 164:1925-1933, 2000; Xu et al., *Cell Immunol* 200:16-26, 2000; Idusogie et al, *J Immunol* 166:2571-2575, 2001; Shields et al., *J Biol Chem* 276:6591-6604, 2001; Jefferis et al, *Immunol Lett* 82:57-65. 2002; Presta et al., *Biochem Soc Trans* 30:487-490, 2002; Lazar et al., *Proc. Natl. Acad. Sci. USA* 103:4005-4010, 2006; U.S. Pat. Nos. 5,624, 821; 5,885,573; 5,677,425; 6,165,745; 6,277,375; 5,869,046; 6,121,022; 5,624,821; 5,648,260; 6,194,551; 6,737,056; 6,821,505; 6,277,375; 7,335,742; and 7,317,091; and PCT Publications WO 94/2935; WO 99/58572; WO 00/42072; WO 02/060919, and WO 04/029207.

In some embodiments, the natural glycosylation of Fc regions may be modified. For example, a modification may be aglycosylation, for example, by removing one or more sites of glycosylation within the antibody sequence. Such an approach is described in further detail in U.S. Pat. Nos. 5,714, 350 and 6,350,861. An Fc region can also be made that has an altered type of glycosylation, such as a hypofucosylated Fc variant having reduced amounts of fucosyl residues or an Fc variant having increased bisecting GlcNAc structures. Such carbohydrate modifications can be accomplished by, for example, expressing the antibody in a host cell with altered glycosylation machinery. Cells with altered glycosylation pathways, including mammalian cells, yeast and plants, have been described in the art and can be used as host cells in which to express recombinant antibodies of the invention to thereby produce an antibody with altered glycosylation. Techniques for modifying glycosylation include those disclosed e.g., in Umana et al, *Nat. Biotechnol* 17:176-180, 1999; Davies, et al., *Biotechnol. Bioeng.* 74:288-294, 2001; Shields et al, *J Biol Chem* 277:26733-26740, 2002; Shinkawa et al., *J Biol Chem* 278:3466-3473, 2003; Niwa et al. *Clinc. Cancer Res.* 1-:6248-6255, 2004; Presta et al., *Biochem Soc Trans* 30:487-490, 2002; Kanda et al, *Glycobiology* 17:104-118, 2006; U.S. Pat. Nos. 6,602,684; 6,946,292; and 7,214,775; U.S. Patent Application Publication Nos. 20070248600; 20070178551; 20080060092; 20060253928; PCT publications WO 00/61739; WO 01/292246; WO 02/311140; and WO 02/30954; and Potelligent™ technology (Biowa, Inc. Princeton, N.J.); and GlycoMAb™ glycosylation engineering technology (GLYCART biotechnology AG, Zurich, Switzerland). Non-glycosylated antibodies may also be produced using ProBioGen technology (von Horsten et al., *Glycobiology* 20(12): 1607-1618, 2010). In a hypofucosylated antibody preparation, typically at least 50 to 70% of the antibody molecule, often at least 80% of the molecules, or at least 90% of the molecules, lack fucose.

In some embodiments of the invention, the antibody is additionally engineered to reduce immunogenicity, e.g., so that the antibody is suitable for repeat administration. Methods for generating antibodies with reduced immunogenicity include humanization and humaneering procedures and modification techniques such as de-immunization, in which an antibody is further engineered, e.g., in one or more framework regions, to remove T cell epitopes.

In some embodiments, the antibody is a HUMANEERED™ antibody. A HUMANEERED™ antibody is an engineered human antibody having a binding specificity of a reference antibody, obtained by joining a DNA sequence encoding a binding specificity determinant (BSD) from a CDR, typically a CDR3 of the heavy chain of the reference antibody to human $V_H$ segment sequences, and a BSD from a CDR, typically a CDR3, of the light chain of the reference antibody to human $V_L$ segment sequences. Methods for generating such antibodies are provided in U.S. Pat. No. 7,981,843 and U.S. Patent Application Publication No. 20060134098.

An antibody can further be de-immunized to remove one or more predicted T-cell epitopes from the V-region of an antibody. Such procedures are described, for example, in WO 00/34317.

In some embodiments, the variable region is comprised of human V-gene sequences. For example, a variable region sequence can have at least 80% identity, or at least 85% or at least 90% identity, or higher, to human germ-line V-gene sequences.

An antibody used in the invention can include a human constant region. The constant region of the light chain may be a human kappa or lambda constant region. The heavy chain constant region is often a gamma chain constant region, for example, a gamma-1 or gamma-3 constant region.

ficity. The ability of a particular antibody to recognize the same epitope as another antibody is typically determined by such competition assays.

A first antibody is considered to competitively inhibit binding of a second antibody, if binding of the second antibody to the antigen is reduced by at least 30%, usually at least about 40%, 50%, 60% or 75%, and often by at least about 90%, in the presence of the first antibody using any of the assays described above.

In some embodiments, the antibody binds to the same epitope as mAb IIIA4. The epitope for mAb IIIA4 and human engineered derivatives resides in the N-terminal globular ligand binding domain of EphA3 (amino acids 29-202 in the partial human EphA3 sequence below):

```
  1 MDCQLSILLL LSCSVLDSFG ELIPQPSNEV NLLDSKTIQG ELGWISYPSH GWEEISGVDE

61 HYTPIRTYQV CNVMDHSQNN WLRTNWVPRN SAQKIYVELK FTLRDCNSIP LVLGTCKETF

121 NLYYMESDDD HGVKFREHQF TKIDTIAADE SFTQMDLGDR ILKLNTEIRE VGPVNKKGFY

181 LAFQDVGACV ALVSVRVYFK KC
```

In some embodiments, e.g., where the antibody is a fragment, the antibody can be conjugated to another molecule, e.g., to provide an extended half-life in vivo such as a polyethylene glycol (pegylation) or serum albumin. Examples of PEGylation of antibody fragments are provided in Knight et al., *Platelets* 15:409, 2004 (for abciximab); Pedley et al., *Br. J. Cancer* 70:1126, 1994 (for an anti-CEA antibody); and Chapman et al., *Nature Biotech.* 17:780, 1999.

Antibody Specificity

An antibody for use in the methods of the invention activates EphA3 and/or kills EphA3+ cells by ADCC. An example of an antibody suitable for use with the present invention is an antibody that has the binding specificity of mAb IIIA4. The monoclonal antibody mAb IIIA4 binds to the native EphA3 globular ephrin-binding domain (Smith et al., *J. Biol. Chem.* 279:9522-9531, 2004; and Vearing et al., *Cancer Res.* 65:6745-6754, 2005). High affinity mAb IIIA4 binding to the EphA3 surface has little effect on the overall affinity of ephrin-A5 interactions with EphA3.

In some embodiments, a monoclonal antibody that competes with mAb IIIA4 for binding to EphA3, or that binds the same epitope as mAb IIIA4, is used. Any of a number of competitive binding assays can be used to measure competition between two antibodies for binding to the same antigen. For example, a sandwich ELISA assay can be used for this purpose. In an exemplary assay, ELISA is carried out by using a capture antibody to coat the surface of a well. A subsaturating concentration of tagged-antigen is then added to the capture surface. This protein will be bound to the antibody through a specific antibody:antigen interaction. After washing, a second antibody that is linked to a detectable moiety is added to the ELISA. If this antibody binds to the same site on the antigen as the capture antibody, or interferes with binding to that site, it will be unable to bind to the target protein as that site will no longer be available for binding. If however this second antibody recognizes a different site on the antigen it will be able to bind. Binding can be detected by quantifying the amount of detectable label that is bound. The background is defined by using a single antibody as both capture and detection antibody, whereas the maximal signal can be established by capturing with an antigen specific antibody and detecting with an antibody to the tag on the antigen. By using the background and maximal signals as references, antibodies can be assessed in a pair-wise manner to determine speci- The mAb IIIA4 antibody binds adjacent to but does not interfere substantially with binding of EphrinA5 to the receptor. The epitope for mAb IIIA4 has been further characterized by Smith et al., *J. Biol. Chem.* 279: 9522, 2004 using site-directed mutagenesis. In this analysis, mutation of Glycine at position 132 to Glutamic acid (G132E) abolishes binding to mAb IIIA4. Mutation of Valine 133 to Glutamic acid (V133E) reduces binding of EphA3 to mAb IIIA4 antibody approximately 100-fold. It has subsequently been observed by the inventors that Arginine 136 is also part of the epitope. This residue is changed to Leucine in the sequence of the highly conserved EphA3 protein in the rat (R136L). Rat EphA3 does not bind mAb IIIA4 or a human engineered derivative of mAb IIIA4. Thus, G132, V133 and R136 (bolded and underlined in the sequence above) are important amino acids within the mab IIIA4 epitope.

Binding Affinity

In some embodiments, the antibodies suitable for use with the present invention have a high affinity binding for human EphA3. For the purposes of this invention, high affinity binding between an antibody and an antigen exists if the dissociation constant ($K_D$) of the antibody is <about 10 nM, for example, about 5 nM, or about 2 nM, or about 1 nM, or less. A variety of methods can be used to determine the binding affinity of an antibody for its target antigen such as surface plasmon resonance assays, saturation assays, or immunoassays such as ELISA or RIA, as are well known to persons of skill in the art. An exemplary method for determining binding affinity is by surface plasmon resonance analysis on a BIAcore™ 2000 instrument (Biacore AB, Freiburg, Germany) using CM5 sensor chips, as described by Krinner et al., (2007) *Mol. Immunol. February;* 44(5):916-25. (Epub 2006 May 11)).

The therapeutic anti-EphA3 antibody can bind to any extracellular region of EphA3. In some embodiments, the anti-EphA3 antibody activates EphA3. Often, the antibody multimerizes, e.g., dimerizes, EphA3. In some embodiments, the antibody clusters EphA3. In some embodiments, an anti-EphA3 antibody can also be employed that has an active isotype, such as an IgG1, IgG3, IgM, IgA, or IgE, and is cytotoxic to hematological proliferative disorder cells via ADCC. Antibodies for use in the invention can also be multivalent including forms of monomers that are cross-linked or otherwise multimerized to form multivalent antibodies.

In some embodiments, an antibody employed in the invention does not compete with an EphA3 ligand for binding to EphA3, whereas in other embodiments an EphA3 antibody for use in the invention can compete for binding of an EphA3 ligand such as an ephrin, e.g., ephrin-A5, to EphA3. Antibodies that compete with a ligand for binding to EphA3, can be identified using techniques as described above, where an ephrin ligand such as ephrin-A5, is used instead of another antibody for a competition analysis.

In exemplary embodiments, the anti-EphA3 antibody comprises the $V_L$ and $V_H$ regions of mAb IIIA4. In other embodiments, the anti-EphA3 antibody comprises CDRs 1, 2 and 3 of mAb IIIA4. In some embodiments, the anti-EphA3 antibody comprises CDR3 of mAb IIIA4. Table 1 provides CDR sequences (defined according to Kabat numbering) of antibodies that bind to the same epitope as mAb IIIA4. Affinity for EphA3 antigen was determined by ELISA. An antibody of the invention may thus also have heavy chain and/or lights chain CDRs set forth in Table 1.

vasculature. Antibodies suitable for use in immunohistochemistry bind to EphA3 subjected to formaldehyde fixation, paraffin embedding and xylene and ethanol extraction. Antibodies for use in IHC are selective for EphA3 and can bind to any region of the EphA3 protein including the extracellular domain or the intracellular domain. Polyclonal and or monoclonal antibodies are suitable for use in this aspect of the invention. In some embodiments the antibody is a monoclonal antibody such as a mouse monoclonal anti-EphA3 antibody. Preferably, the antibody chosen for immunohistochemistry binds to a different epitope from that recognized by a therapeutic antibody. In some embodiments, the antibody for detection of EphA3 expression binds to a different epitope from that recognized by monoclonal antibody IIIA4 and does not compete with mAb IIIA4 for binding to EphA3.

In some embodiments, the antibody for detecting Epha3 expression is SL-2, which is produced by a hybridoma deposited with the ATCC having the accession number PTA-12227;

TABLE 1

| antibody | CDRH1 (SEQ ID NO:) | CDRH2 (SEQ ID NO:) | CDRH3 (SEQ ID NO:) | AFFINITY (nM) |
|---|---|---|---|---|
| IIIA4 | SYWIN (2) | DIYPGSGNTNYDEKFKR (3) | SGYYEDFDS (4) | 2.5 |
| FA3AM-H12 | ATYWIS (5) | DIYPGSGNTNYDEKFQG (6) | SGYYEEFDS (7) | 3.2 |
| K3D | TYWIS (5) | DIYPGSGNTNYDEKFEG (8) | SGYYEEFDS (7) | 25 |

| antibody | CDRL1 (SEQ ID NO:) | CDRL2 (SEQ ID NO:) | CDRL3 (SEQ ID NO:) | AFFINITY (nM) |
|---|---|---|---|---|
| IIIA4 | RASQEISGYLG (9) | AASTLDS (10) | VQYANYPYT (11) | 2.5 |
| FA3AM-H12A | RASQGIISYLA (12) | AASSLQS (13) | VQYANYPYT (11) | 3.2 |
| K3D | RASQGIISYLA (12) | AASSLQS (13) | VQYMNYPYT (14) | 25 |

Examples of therapeutic antibodies for use in the invention are described, e.g., in WO2011/053465, which is incorporate by reference.

Antibodies as described herein for use in the invention can be identified using known assays for the characteristic of interest. Thus, antibodies can be identified by screening for the ability to activate EphA3 (e.g., using a phosphorylation assay and/or screening for changes in cell morphology, such as rounding), the ability to induce ADCC, and for binding specificity and affinity. Such assays are well known in the art.

Diagnostic Antibodies

Therapeutic antibodies may also be used for diagnosis. Accordingly, any of the antibodies described above may be employed for identifying EphA3 expression on aberrant vasculature.

Anti-EphA3 antibodies that bind to a region other than the extracellular domain may also be used for detecting EphA3 expression. For example, 5E11F2 (commercially available from Invitrogen) binds to the C-terminal peptide amino acids 955-983 and can be used diagnostically. For the purposes of detecting EphA3 expression, antibodies are employed in a format that can bind to EphA3 present on the vasculature.

In typical embodiments the antibody is used for immuno-histochemical analysis of EphA3 expression on bone marrow or SL-7, which is produced by a hybridoma deposited with the ATCC having the accession number PTA-12228.

The invention also provides a monoclonal antibody, e.g., SL-2 or SL-7, that can be used to detect EphA3 expression on aberrant vasculature; and kits that contain the antibody. A kit of the invention includes an SL-2 or SL-7 antibody, or both, and may include other reagents for analyzing expression, e.g., a secondary antibody, buffers, and other reagents.

Non Antibody EphA3 Binding Agents for Therapy

Other proteins that bind to EphA3 and dimerize or activate EphA3 receptor may also be administered to a patient that has a hematological proliferative disorder where the hematological proliferative disorder cells do not express or minimally express EphA3. Such proteins include a soluble Ephrin A5-Fc protein.

Other EphA3 binding agents include scaffolded proteins that bind EphA3. Thus, the EphA3 binding agent can be an "antibody mimetic" that targets and binds to the antigen in a manner similar to antibodies. When an antibody mimetic is used, the form of the mimetic is such that it multimerizes EphA3. For example, the antibody mimetic may be used in a dimeric or multivalent format.

Certain antibody mimetics use non-immunoglobulin protein scaffolds as alternative protein frameworks for the variable regions of antibodies. For example, Ku et al. (*Proc. Natl. Acad. Sci. U.S.A.* 92:6552-6556, 1995) discloses an alternative to antibodies based on cytochrome b562 in which two of the loops of cytochrome b562 were randomized and selected for binding against bovine serum albumin. The individual mutants were found to bind selectively with BSA similarly with anti-BSA antibodies.

U.S. Pat. Nos. 6,818,418 and 7,115,396 disclose an antibody mimetic featuring a fibronectin or fibronectin-like protein scaffold and at least one variable loop. Known as Adnectins, these fibronectin-based antibody mimics exhibit many of the same characteristics of natural or engineered antibodies, including high affinity and specificity for any targeted ligand. The structure of these fibronectin-based antibody mimics is similar to the structure of the variable region of the IgG heavy chain. Therefore, these mimics display antigen binding properties similar in nature and affinity to those of native antibodies. Further, these fibronectin-based antibody mimics exhibit certain benefits over antibodies and antibody fragments. For example, these antibody mimics do not rely on disulfide bonds for native fold stability, and are, therefore, stable under conditions which would normally break down antibodies. In addition, since the structure of these fibronectin-based antibody mimics is similar to that of the IgG heavy chain, the process for loop randomization and shuffling may be employed in vitro that is similar to the process of affinity maturation of antibodies in vivo.

Beste et al. (*Proc. Natl. Acad. Sci. U.S.A.* 96:1898-1903, 1999) disclose an antibody mimic based on a lipocalin scaffold (Anticalin®). Lipocalins are composed of a β-barrel with four hypervariable loops at the terminus of the protein. The loops were subjected to random mutagenesis and selected for binding with, for example, fluorescein. Three variants exhibited specific binding with fluorescein, with one variant showing binding similar to that of an anti-fluorescein antibody. Further analysis revealed that all of the randomized positions are variable, indicating that Anticalin® would be suitable to be used as an alternative to antibodies. Thus, Anticalins® are small, single chain peptides, typically between 160 and 180 residues, which provides several advantages over antibodies, including decreased cost of production, increased stability in storage and decreased immunological reaction.

U.S. Pat. No. 5,770,380 discloses a synthetic antibody mimetic using the rigid, non-peptide organic scaffold of calixarene, attached with multiple variable peptide loops used as binding sites. The peptide loops all project from the same side geometrically from the calixarene, with respect to each other. Because of this geometric confirmation, all of the loops are available for binding, increasing the binding affinity to a ligand. However, in comparison to other antibody mimics, the calixarene-based antibody mimic does not consist exclusively of a peptide, and therefore it is less vulnerable to attack by protease enzymes. Neither does the scaffold consist purely of a peptide, DNA or RNA, meaning this antibody mimic is relatively stable in extreme environmental conditions and has a long life span. Further, since the calixarene-based antibody mimic is relatively small, it is less likely to produce an immunogenic response.

Murali et al. (*Cell Mol Biol* 49:209-216, 2003) describe a methodology for reducing antibodies into smaller peptidomimetics, they term "antibody like binding peptidomimetics" (ABiP) which may also be useful as an alternative to antibodies.

WO 00/60070 discloses a polypeptide chain having CTL4A-like β-sandwich architecture. The peptide scaffold has from 6 to 9 β-strands, wherein two or more of the polypeptide β-loops constitute binding domains for other molecules, such as antigen binding fragments. The basic design of the scaffold is of human origin, thus reducing the risk of inducing an immune response. The β-sandwich scaffold may have improved stability and pharmacokinetic properties in vivo when compared to standard antibodies as the molecule contains a second, non-immunoglobulin disulphide bridge. As antigen binding domains can be located at opposite ends of a single peptide chain, the β-sandwich also facilitates design of bispecific monomeric molecules.

In addition to non-immunoglobulin protein frameworks, antibody properties have also been mimicked in compounds comprising RNA molecules and unnatural oligomers (e.g., protease inhibitors, benzodiazepines, purine derivatives and beta-turn mimics). Accordingly, non-antibody EphA3 binding agents can also include such compounds.

In some embodiments, the EphA3 binding agents employed in the invention competed with mAb IIIA4 for binding to EphA3. Such agents can be identified using known assays, such as the exemplary competition assays described herein.

Identification of Patients who are Candidate for Treatment with anti-EphA3

The invention also provides methods of determining whether a patient having a hematological proliferative disorder is a candidate for treatment with an anti-EphA3 antibody. The methods comprise detecting the expression of EphA3 on aberrant bone marrow vasculature in the patient.

EphA3 expression can be detected using methods well known in the art. Often, an immunological assay employing immunohistochemistry is used to detect EphA3 expression on aberrant bone marrow vasculature. Alternatively EphA3 expression can be detected by detecting mRNA encoding EphA3 in the aberrant bone marrow vasculature. For example, a nucleic acid amplification method that comprises RT-PCR may be employed.

In evaluating a patient that is a candidate for treatment, a bone marrow sample comprising hematological proliferative disorder cells is obtained from the patient for evaluating EphA3 expression. A patient is considered to be a candidate for treatment with an anti-EphA3 antibody if the aberrant vasculature expresses EphA3. Accordingly, "an EphA3+ patient" as used here is a hematological proliferative disorder patient that shows EphA3 expression aberrant bone marrow vasculature.

Treatment of Hematological Proliferative Disorders

In one aspect, the methods of the present invention comprise administering an anti-EphA3 agent, typically an anti-EphA3 antibody, to a patient that has a hematological proliferative disorder that has aberrant bone marrow vasculature that expresses EphA 3, but has EphA3-hematological proliferative disorder cell expression. In some embodiments, an anti-EphA3 agent, such as an antibody, is administered to the patient. In some embodiments, the patient has AML. In some embodiments, the patient has CML, CMML, JMML, MDS, PV, ET, or IM. In some embodiments, the patient has CLL, MM, diffuse large B-cell lymphoma, NHL, MCL, chronic neutrophilic leukemia, chronic eosinophilic leukemia, or mast cell disease.

Various methods, including immunological methods such as flow cytometry and PCR methods can be employed to identify whether hematological proliferative disorder cells express EphA3. Leukemic and other hematological proliferative disorder cells can be identified by commonly used techniques such as immunophenotyping using flow cytometry, or by in vitro cell culture techniques or in vivo transplantation experiments.

Stem cells are multipotent progenitor cells that may be further defined functionally as cells with self-renewing capacity (see, e.g., Reya et al., *Nature* 414:105-111, 2001, and references cited therein). This may be demonstrated, for example, in long-term culture initiating cell (LTC-IC) assays in which cells are cultured on irradiated bone-marrow stromal feeder cells. In this assay, the presence of stem cells is revealed by the ability to serially transfer colonies for extended periods (e.g., at least 5 weeks e.g. Guan and Hogge (2000) Leukemia 14: 2135). Serial transfer assays may also be carried out by culturing stem cell-derived colonies in methyl cellulose in the presence of growth factors, such as a combination of stem cell factor (SCF), interleukin-3 (IL3), granulocyte macrophage colony stimulating factor (GM-CSF) and erythropoietin (EPO).

In vivo transplantation to identify stem cells is carried out by passaging by serial transfer in mice with defective immune systems (SCID/NOD mice; van Rhenen et al., *Clin. Cancer. Res.* 11: 6520-6527, 2005).

In flow cytometry analysis, leukemic or chronic myeloproliferative disorder (CMPD) stem cells are typically present in the CD34-positive, CD38-negative cell compartment (although approximately 10% of AML cases are CD34-negative). Leukemic or CMPD stem cells can be identified in the CD38-negative cell compartment as CD123-positive cells (Jordan et al., *Leukemia* 14: 1777-1784, 2000) although other markers may also be used to identify stem cells including the presence of CD117, CD45RA or CD133.

Blast cells are unipotent cells that are able to participate in granulopoiesis. Blast cells are larger cells than normal human mononuclear and polymorphonuclear blood cells and can be identified by microscopy from blood smears or by flow cytometry analysis on the basis of high forward scatter (FSC) and side scatter (SSC) compared with monocytes and granulocytes.

The anti-EphA3 composition for administering to the patient can be formulated for use in a variety of drug delivery systems. One or more physiologically acceptable excipients or carriers can also be included in the compositions for proper formulation. Suitable formulations for use in the present invention are found in *Remington: The Science and Practice of Pharmacy*, 21st Edition, Philadelphia, Pa. Lippincott Williams & Wilkins, 2005. For a brief review of methods for drug delivery, see, Langer, *Sciences* 249: 1527-1533 (1990).

The anti-EphA3 antibody for use in the methods of the invention is provided in a solution suitable for injection into the patient such as a sterile isotonic aqueous solution for injection. The anti-EphA3 antibody is dissolved or suspended at a suitable concentration in an acceptable carrier. In some embodiments the carrier is aqueous, e.g., water, saline, phosphate buffered saline, and the like. The compositions may contain auxiliary pharmaceutical substances as required to approximate physiological conditions, such as pH adjusting and buffering agents, tonicity adjusting agents, and the like.

The pharmaceutical compositions of the invention are administered to a patient that has a hematological proliferative disorder in which aberrant bone marrow vasculature expresses EphA3, but the hematological proliferative disorder cells do not, in an amount sufficient to at least partially arrest the disease or symptoms of the disease and its complications. An amount adequate to accomplish this is defined as a "therapeutically effective dose." A therapeutically effective dose is determined by monitoring a patient's response to therapy. Typical benchmarks indicative of a therapeutically effective dose are known in the art, depending on the disease. For example, therapeutic efficacy may be indicated by the decrease of the number of abnormal myeloid cells that are characteristic of the particular myeloid proliferation disorder in the blood or bone marrow.

The dose of the anti-EphA3 antibody is chosen in order to provide effective therapy for the patient and is in the range of about 0.1 mg/kg body weight to about 10 mg/kg body weight or in the range about 1 mg to about 1 g per patient. The dose is often in the range of about 0.5 mg/kg or about 1 mg/kg to about 10 mg/kg, or approximately about 50 mg to about 1000 mg/patient. In some embodiments, the antibody is administered in an amount less than about 0.1 mg/kg body weight, e.g., in an amount of about 20 mg/patient or less. The dose may be repeated at an appropriate frequency which may be in the range once per day to once every three months, depending on the pharmacokinetics of the antibody (e.g. half-life of the antibody in the circulation) and the pharmacodynamic response (e.g. the duration of the therapeutic effect of the antibody). In some embodiments where the antibody or modified antibody fragment has an in vivo half-life of between about 7 and about 25 days and antibody dosing is repeated between once per week and once every 3 months. In other embodiments, the antibody is administered approximately once per month.

Amounts that are administered that are effective will depend upon the severity of the disease and the general state of the patient's health, including other factors such as age, weight, gender, administration route, etc. Single or multiple administrations of the anti EphA3 antibody may be administered depending on the dosage and frequency as required and tolerated by the patient. In any event, the methods provide a sufficient quantity of the anti EphA3 antibody to effectively treat the hematological proliferative disorder.

An anti-EphA3 antibody or anti-EphA3 agonist binding agent, e.g., that induces multimerization or activates EphA3, can be used in combination with one or more additional therapeutic agents to treat the hematological proliferative disorder. Therapeutic agents that can be administered in conjunction with anti-EphA3 binding agents include compounds such as MYLOTARG® (gemtuzumab ozogamicin for injection); a tyrosine kinase inhibitor such as imatinib mesylate (GLEEVEC®), nilotinib (TASIGNA®), and dasatinib (SPRYCEL®); interferon-α, and various chemotherapeutic agents.

In some embodiments, an anti-EphA3 activating antibody can be used in combination with one or more additional therapeutic agents to treat a patient that has chronic myeloid leukemia where leukemic stem cells from the patient express EphA3. Such therapeutic agents include various chemotherapeutic agents and imatinib mesylate (GLEEVEC®).

In some embodiments, an anti-EphA3 antibody, e.g., an activating antibody, can be used in combination with one or more additional agents to treat acute myeloid leukemia. Such agents include cytosine arabinoside alone and in combination with daunorubicin.

In some embodiments, an anti-EphA3 activating antibody can be used in combination with one or more additional therapeutic agents to treat a patient that has a BCR-ABL negative CMPD. Such inhibitors include JAK2 inhibitors, which are known in the art and undergoing clinical evaluation.

Patients can receive one or more of these additional therapeutic agents as concomitant therapy. Alternatively, patients may be treated sequentially with additional therapeutic agents.

In some embodiments, an anti-EphA3 activating antibody is administered to a patient that has undergone a bone marrow transplant, where the patient has hematological proliferative disorder cells that are negative for EphA3 expression.

In some embodiments, an anti-EphA3 antibody, or other activating Epha3 binding agent, is administered by injection or infusion through any suitable route, typically intravenous routes. In some embodiments, the anti-EphA3 antibody is diluted in a physiological saline solution for injection prior to administration to the patient. The antibody is administered, for example, by intravenous infusion over a period of between 15 minutes and 2 hours.

The following examples are provided by way of illustration only and not by way of limitation. Those of skill in the art will readily recognize a variety of non-critical parameters that could be changed or modified to yield essentially similar results.

EXAMPLES

Example 1

Identification of an Anti-EphA3 Monoclonal Antibody for Use in Immunohistochemistry A panel of monoclonal antibodies that bind the extracellular domain of EphA3 were generated by immunization of mice with human EphA3-Fc fusion protein. Spleen cells from immunized mice were fused with the SP2/0 hybridoma. Supernatants from seven hybridomas (named SL-1-SL-7), each secreting a murine IgG1 isotype monoclonal antibody, were assayed for EphA3 binding by ELISA (FIG. 1). ELISA plates (Costar, cat #3590) were coated with 50 ng/well of EphA3-Fc for 1 hr at 37° C. Wells were washed once with phosphate-buffered saline with 0.1% Tween 20 (PBST) and blocked with 5% Skimmed Milk (Marvel) in PBST for 1 hr at 37° C. Following one wash with PBST, a two-fold dilution series of antibody supernatant in PBS (50 µl/well) was added across the plates (10 dilutions). The plates were incubated for 1 hr at RT. Plates were washed 3× with PBST and 100 µl of a 1:2000 dilution of goat anti-mouse HRP (DAKO, cat #P0447) was added to each well. Plates were incubated for 45 minutes at RT. Plates were washed 3× in PBST, 1× in PBS and developed with 100 µl/well of TMB reagent (Sigma, T0440-1L). Reactions were stopped with 100 µl of 2M H2SO4 and absorbance measured at 450 nm (Spectramax Plus, Molecular Devices). Antibody concentrations in the supernatants were quantified by biolayer interferometry using a ForteBio Octet biosensor.

Each of the antibodies bound to recombinant EphA3. SL-2 antibody had the highest affinity (EC50=0.24 nM).

Four antibodies with the highest affinity, SL-2, SL-5, SL-6 and SL-7 were tested for cross reactivity with other Ephs. ELISA plates were coated with 6 different Ephs (EphA1, EphA2, EphA3, EphA5, EphB4 and EphB6) and probed with SL-2, SL-5, SL-6 and SL-7. All four antibodies bound EphA3 specifically and showed no detectable binding to other Eph proteins or Fc-fusion proteins.

Antibodies were purified from hybridoma supernatant using Protein A affinity chromatography. Cell supernatant in the range 0.7-4.2 liters was loaded onto a 25 mL rProtein A FF column (GE Healthcare) at 3.7 mL/min at 4° C. with the pump P-50 (GE Healthcare). After loading the cell supernatant, the column was transferred to an ÄKTA Prime Purification System (GE Healthcare), washed with 10 column volumes of Buffer A (PBS pH7.0) at a flow-rate of 4 mL/min. Antibody was eluted from the column with Buffer B (0.3M Arg, 0.15M NaCl pH 2.8) in 9 mL fractions. Each fraction was neutralized with 1 mL 2M Tris pH 8.0. Fractions containing antibody were identified by SDS-PAGE (4-20% Tris-Glycine Gel; Invitrogen; Cat #EC60252). Selected fractions were pooled and buffer exchanged into 1×PBS pH 7.0 overnight at 4° C. using a Slide-A-Lyze dialysis cassette (ThermoFisher; Cat #17-5080-01). Following the buffer exchange, the sample was removed from the dialysis cassette and filtered through a 0.22 um filter.

Binding of purified monoclonal antibodies to native EphA3 expressed on the cell surface was confirmed by flow cytometry using EphA3-positive cell line LK63. For flow cytometry analysis, LK63 cells were harvested by centrifugation at 200 g for 5 minutes, washed once in dPBS (Invitrogen, cat #14190) and blocked with 2% bovine serum albumin (BSA)+10 µg/ml rat IgG in dPBS for 25 minutes on ice. Cells were incubated with 25 nM purified anti-EphA3 antibodies for 30 minutes on ice, washed once in cold dPBS+0.5% BSA, and incubated in a 1:100 dilution of FITC-conjugated anti-mouse secondary antibody (Jackson Immunoresearch 115-096-062) for 20 minutes on ice. Cells were washed once in cold dPBS+0.5% BSA before being re-suspended in 0.5 ml cold dPBS for FACS analysis. Propidium iodide (1 µl/sample, Sigma cat #P4864) was used to exclude non-viable cells from FITC channel readings and flow cytometry was carried out using a FACSCaliber instrument (Beckton Dickinson).

Figure 2:
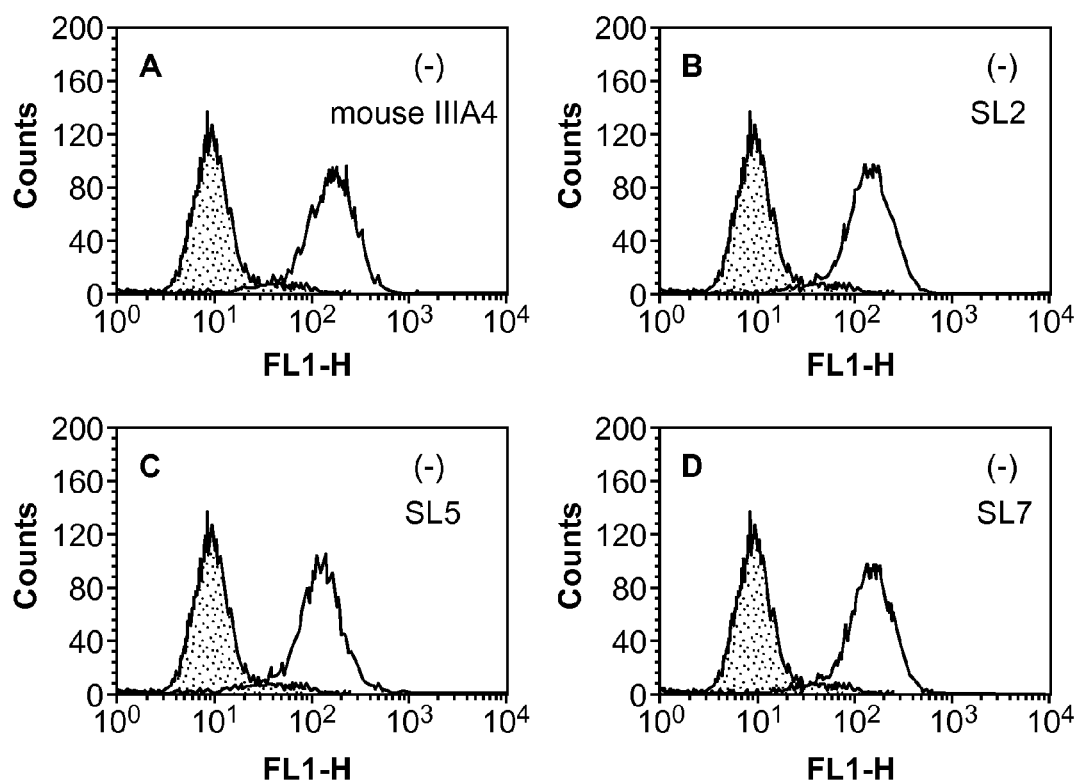
FIG. 2 provides illustrative data that shows binding of purified SL antibodies to LK63 cells analyzed by FACS. Binding of antibodies is shown (open histogram) in comparison with an irrelevant isotype control antibody (filled histogram) (A) 25 nM mouse mAb IIIA4, (B) 25 nM SL-2, (C) 25 nM SL-5, and D) 25 nM SL-7 antibodies to LK63 cells is shown. Data for each sample represents 10,000 events excluding dead cells.

As shown in FIG. 2, purified SL-2, SL-5, and SL-7 antibodies bound to LK63 cells at levels equivalent to the mouse IIIA4 anti-EphA3 positive control antibody.

Example 2

Expression of EphA3 on AML Tumor Vasculature

Standard bone-marrow biopsy formaldehyde-fixed paraffin embedded (FFPE) sections were used for analysis of binding of anti-EphA3 antibodies to cells in the bone marrow of AML patients by immunohistochemistry. Sections were treated in two changes of xylene (5 minutes each) to remove paraffin, hydrated through an ethanol series and rinsed in distilled water. Antigen retrieval was performed using Proteinase K (IHC world, Cat #IW-1101) for 10 minutes at 37° C. in humidified chamber followed by rinsing in Tris-buffered saline pH7.4 with 0.1% Tween 20 (TBST) for 4 minutes. Slides were blocked using universal blocking solution (Vector Laboratories Inc., Cat #SP-2001) for 10 minutes followed by Avidin solution for 15 minutes and biotin solution for 15 minutes. Fresh antibody blocking solution (0.07 g skimmed milk, +210 ul goat serum, +14 ml antibody diluent) was added to the slides for 20 minutes at room temperature and slides were rinsed with TBST. Primary antibodies (SL-2, SL-5 or SL-7) or isotype control antibody were diluted to 25 µg/ml in antibody diluent (IHC World, Cat #IW-1000) and added to slides (0.5 ml per slide) for 1 hour at room temperature. Slides were then rinsed twice in TBST. Biotin-SP-conjugated Goat Anti-Mouse IgG: (Jackson ImmunoResearch Laboratories, Cat #115-065-166) secondary antibody was diluted 1:500 in antibody diluent and added to the slides. Slides were incubated for 30 minutes at room temperature and rinsed twice in TBST. Two to three drops of Phosphatase-Labeled Streptavidin (KPL, Cat #: 71-00-45) was also added and the slides were incubated for 30 minutes at room temperature. After two rinses, New Fuchsin Substrate System (Dako, Cat #K0698) was used according to the manufacturer's instructions to develop the slides.

SL-2 antibody detected EphA3-positive cells in immunohistochemistry in bone marrow from human AML patients. In AML bone marrow (Table 2), EphA3 was detected on the endothelium in tumor neovasculature. In larger blood vessels such as arterioles, EphA3 was expressed in vessel tissues adjacent to the endothelial layer. In contrast, EphA3 was not detected in normal bone marrow.

TABLE 2

Detection of EphA3 in biopsy tissue sections from normal bone marrow or bone marrow from AML patients by immunohistochemistry using SL-2 monoclonal antibody. Patient disease sub-type is scored using the Fench American British (FAB) classification scheme.

| Sample | FAB sub-type, Stage | Hematopoietic cells | Blood vessels |
|---|---|---|---|
| I-6414 | normal | − | − |
| I-1360 | normal | − | − |
| 7709 | M6 | + | + |
| 7703 | M5a | − | − |
| 7706 | M1 | − | − |
| I-8930 | M1 (CD34−ve) | + | + |
| I-8931 | M5a | + | + |
| 7704 | n/a, relapse | − | + |
| 7710 | M1 | − | − |
| 7707 | n/a, relapse | + | + |
| 7708 | M3 | − | + |
| 7712 | M2 | − | + | n/a denotes not identified.

All publications, patent applications, accession numbers, and other references cited in this specification are herein incorporated by reference as if each individual publication or patent application were specifically and individually indicated to be incorporated by reference.

What is claimed is:

1. A method of treating a patient that has a hematological proliferative disorder where less than 20% of the hematological proliferative disorder cells express EphA3, and aberrant vasculature in bone marrow is EphA3+, the method comprising administering a therapeutically effective amount of an anti-EphA3 antibody to the patient, wherein the anti-EphA3 antibody (i) activates EphA3 and/or (ii) induces ADCC.

2. The method of claim 1, wherein 5% or less of the hematological proliferative disorder cells express EphA3 and the hematological proliferative disorder is acute myeloid leukemia (AML).

3. The method of claim 1, wherein 5% or less of the hematological proliferative disorder cells express EphA3 and the hematological proliferative disorder is chronic myeloid leukemia (CML), chronic myelomonocytic leukemia (CMML), juvenile myelomonocytic leukemia (JMML), myelodysplastic syndrome (MDS), polycythemia vera (PV), essential thrombocythemia (ET), or idiopathic myelofibrosis (IM).

4. The method of claim 1, wherein the hematological proliferative disorder is chronic lymphocytic leukemia, multiple myeloma, diffuse large B-cell lymphoma, non-Hodgkin lymphoma, mantle cell lymphoma, chronic neutrophilic leukemia, chronic eosinophilic leukemia, or mast cell disease.

5. The method of claim 1, wherein the anti-EphA3 antibody comprises a human heavy chain gamma-1 or gamma-3 constant region.

6. The method of claim 1, wherein the anti-EphA3 antibody is provided in a hypofucosylated or afucosylated antibody preparation.

7. The method of claim 1, wherein the anti-EphA3 antibody induces ADCC.

8. The method of claim 1, wherein the anti-EphA3 antibody blocks binding of ephrinA5 ligand to EphA3.

9. The method of claim 1, wherein the anti-EphA3 antibody binds to the epitope on EphA3 to which an antibody having a $V_H$ region CDR1 having a sequence SYWIN (SEQ ID NO:2), a $V_H$ region CDR2 having a sequence DIYPGSGNTNYDEKFKR (SEQ ID NO:3), a $V_H$ region CDR3 having a sequence SGYYEDFDS (SEQ ID NO:4), a $V_L$ region CDR1 having a sequence RASQEISGYLG (SEQ ID NO:9), a $V_L$ region CDR2 having a sequence AASTLDS (SEQ ID NO:10), and a $V_L$ region CDR3 having a sequence VQYANYPYT (SEQ ID NO:11) binds.

10. The method of claim 1, wherein the anti-EphA3 antibody is a recombinant or chimeric antibody.

11. The method of claim 1, wherein the anti-EphA3 antibody is a humanized or engineered human antibody.

12. The method of claim 1, wherein the anti-EphA3 antibody is a monoclonal antibody.

13. The method of claim 1, wherein the anti-EphA3 antibody is a polyclonal antibody.

14. The method of claim 1, wherein the anti-EphA3 antibody is a multivalent antibody that comprises a Fab, a Fab', or an Fv.

* * * * *

SEQUENCE LISTING

```
<160> NUMBER OF SEQ ID NOS: 14

<210> SEQ ID NO 1
<211> LENGTH: 202
<212> TYPE: PRT
<213> ORGANISM: Artificial Sequence
<220> FEATURE:
<223> OTHER INFORMATION: synthetic N-terminal globular ligand binding
      domain of human Eph receptor A3 (EphA3), human embryo kinase
      (hek), eph-like tyrosine kinase 1 (etk1), tyro4, partial sequence
      including mAb IIIA4 epitope, amino acids 29-202

<400> SEQUENCE: 1

Met Asp Cys Gln Leu Ser Ile Leu Leu Leu Ser Cys Ser Val Leu
 1               5                  10                  15

Asp Ser Phe Gly Glu Leu Ile Pro Gln Pro Ser Asn Glu Val Asn Leu
                20                  25                  30

Leu Asp Ser Lys Thr Ile Gln Gly Glu Leu Gly Trp Ile Ser Tyr Pro
            35                  40                  45

Ser His Gly Trp Glu Glu Ile Ser Gly Val Asp Glu His Tyr Thr Pro
        50                  55                  60

Ile Arg Thr Tyr Gln Val Cys Asn Val Met Asp His Ser Gln Asn Asn
65                  70                  75                  80

Trp Leu Arg Thr Asn Trp Val Pro Arg Asn Ser Ala Gln Lys Ile Tyr
                85                  90                  95

Val Glu Leu Lys Phe Thr Leu Arg Asp Cys Asn Ser Ile Pro Leu Val
                100                 105                 110

Leu Gly Thr Cys Lys Glu Thr Phe Asn Leu Tyr Tyr Met Glu Ser Asp
            115                 120                 125

Asp Asp His Gly Val Lys Phe Arg Glu His Gln Phe Thr Lys Ile Asp
        130                 135                 140

Thr Ile Ala Ala Asp Glu Ser Phe Thr Gln Met Asp Leu Gly Asp Arg
145                 150                 155                 160

Ile Leu Lys Leu Asn Thr Glu Ile Arg Glu Val Gly Pro Val Asn Lys
                165                 170                 175

Lys Gly Phe Tyr Leu Ala Phe Gln Asp Val Gly Ala Cys Val Ala Leu
                180                 185                 190

Val Ser Val Arg Val Tyr Phe Lys Lys Cys
                195                 200
```

```
<210> SEQ ID NO 2
<211> LENGTH: 5
<212> TYPE: PRT
<213> ORGANISM: Artificial Sequence
<220> FEATURE:
<223> OTHER INFORMATION: synthetic anti-EphA3 monoclonal antibody IIIA4
      V-H heavy chain region CDRH1

<400> SEQUENCE: 2

Ser Tyr Trp Ile Asn
1               5

<210> SEQ ID NO 3
<211> LENGTH: 17
<212> TYPE: PRT
<213> ORGANISM: Artificial Sequence
<220> FEATURE:
<223> OTHER INFORMATION: synthetic anti-EphA3 monoclonal antibody IIIA4
      V-H heavy chain region CDRH2

<400> SEQUENCE: 3

Asp Ile Tyr Pro Gly Ser Gly Asn Thr Asn Tyr Asp Glu Lys Phe Lys
1               5                   10                  15

Arg

<210> SEQ ID NO 4
<211> LENGTH: 9
<212> TYPE: PRT
<213> ORGANISM: Artificial Sequence
<220> FEATURE:
<223> OTHER INFORMATION: synthetic anti-EphA3 monoclonal antibody IIIA4
      V-H heavy chain region CDRH3

<400> SEQUENCE: 4

Ser Gly Tyr Tyr Glu Asp Phe Asp Ser
1               5

<210> SEQ ID NO 5
<211> LENGTH: 5
<212> TYPE: PRT
<213> ORGANISM: Artificial Sequence
<220> FEATURE:
<223> OTHER INFORMATION: synthetic anti-EphA3 monoclonal antibody
      FA3AM-H12A and K3D V-H heavy chain region CDRH1

<400> SEQUENCE: 5

Thr Tyr Trp Ile Ser
1               5

<210> SEQ ID NO 6
<211> LENGTH: 17
<212> TYPE: PRT
<213> ORGANISM: Artificial Sequence
<220> FEATURE:
<223> OTHER INFORMATION: synthetic anti-EphA3 monoclonal antibody
      FA3AM-H12A V-H heavy chain region CDRH2

<400> SEQUENCE: 6

Asp Ile Tyr Pro Gly Ser Gly Asn Thr Asn Tyr Asp Glu Lys Phe Gln
1               5                   10                  15

Gly

<210> SEQ ID NO 7
<211> LENGTH: 9
<212> TYPE: PRT
```

```
<213> ORGANISM: Artificial Sequence
<220> FEATURE:
<223> OTHER INFORMATION: synthetic anti-EphA3 monoclonal antibody
      FA3AM-H12A and K3D V-H heavy chain region CDRH3

<400> SEQUENCE: 7

Ser Gly Tyr Tyr Glu Glu Phe Asp Ser
 1               5

<210> SEQ ID NO 8
<211> LENGTH: 17
<212> TYPE: PRT
<213> ORGANISM: Artificial Sequence
<220> FEATURE:
<223> OTHER INFORMATION: synthetic anti-EphA3 monoclonal antibody K3D
      V-H heavy chain region CDRH2

<400> SEQUENCE: 8

Asp Ile Tyr Pro Gly Ser Gly Asn Thr Asn Tyr Asp Glu Lys Phe Glu
 1               5                  10                  15

Gly

<210> SEQ ID NO 9
<211> LENGTH: 11
<212> TYPE: PRT
<213> ORGANISM: Artificial Sequence
<220> FEATURE:
<223> OTHER INFORMATION: synthetic anti-EphA3 monoclonal antibody IIIA4
      V-L light chain region CDRL1

<400> SEQUENCE: 9

Arg Ala Ser Gln Glu Ile Ser Gly Tyr Leu Gly
 1               5                  10

<210> SEQ ID NO 10
<211> LENGTH: 7
<212> TYPE: PRT
<213> ORGANISM: Artificial Sequence
<220> FEATURE:
<223> OTHER INFORMATION: synthetic anti-EphA3 monoclonal antibody IIIA4
      V-L light chain region CDRL2

<400> SEQUENCE: 10

Ala Ala Ser Thr Leu Asp Ser
 1               5

<210> SEQ ID NO 11
<211> LENGTH: 9
<212> TYPE: PRT
<213> ORGANISM: Artificial Sequence
<220> FEATURE:
<223> OTHER INFORMATION: synthetic anti-EphA3 monoclonal antibody IIIA4
      and FA3AM-H12A V-L light chain region CDRL3

<400> SEQUENCE: 11

Val Gln Tyr Ala Asn Tyr Pro Tyr Thr
 1               5

<210> SEQ ID NO 12
<211> LENGTH: 11
<212> TYPE: PRT
<213> ORGANISM: Artificial Sequence
<220> FEATURE:
<223> OTHER INFORMATION: synthetic anti-EphA3 monoclonal antibody
      FA3AM-H12A and K3D V-L light chain region CDRL1

<400> SEQUENCE: 12
```

```
Arg Ala Ser Gln Gly Ile Ile Ser Tyr Leu Ala
 1               5                   10

<210> SEQ ID NO 13
<211> LENGTH: 7
<212> TYPE: PRT
<213> ORGANISM: Artificial Sequence
<220> FEATURE:
<223> OTHER INFORMATION: synthetic anti-EphA3 monoclonal antibody
      FA3AM-H12A and K3D V-L light chain region CDRL2

<400> SEQUENCE: 13

Ala Ala Ser Ser Leu Gln Ser
 1               5

<210> SEQ ID NO 14
<211> LENGTH: 9
<212> TYPE: PRT
<213> ORGANISM: Artificial Sequence
<220> FEATURE:
<223> OTHER INFORMATION: synthetic anti-EphA3 monoclonal antibody K3D
      V-L light chain region CDRL3

<400> SEQUENCE: 14

Val Gln Tyr Met Asn Tyr Pro Tyr Thr
 1               5
```